(12) United States Patent
Gross

(10) Patent No.: US 10,543,083 B2
(45) Date of Patent: Jan. 28, 2020

(54) PROSTHETIC AORTIC VALVE PACING SYSTEM

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 34 days.

(21) Appl. No.: 15/864,661

(22) Filed: Jan. 8, 2018

(65) Prior Publication Data
US 2019/0209302 A1   Jul. 11, 2019

(51) Int. Cl.
  *A61F 2/24*    (2006.01)
  *A61N 1/375*   (2006.01)
  *A61N 1/362*   (2006.01)

(52) U.S. Cl.
  CPC .......... *A61F 2/2418* (2013.01); *A61F 2/2409* (2013.01); *A61N 1/3629* (2017.08); *A61N 1/37512* (2017.08); *A61F 2/2427* (2013.01); *A61F 2210/0014* (2013.01); *A61F 2220/005* (2013.01); *A61F 2220/0075* (2013.01); *A61F 2230/0078* (2013.01); *A61F 2240/001* (2013.01); *A61F 2250/0001* (2013.01); *A61F 2250/008* (2013.01)

(58) Field of Classification Search
  CPC ........ A61F 2/24; A61F 2/2415; A61F 2/2418; A61F 2/2475; A61F 2/2478; A61M 39/00; A61M 1/127; A61M 1/125
  See application file for complete search history.

(56) References Cited

U.S. PATENT DOCUMENTS

| | | | | |
|---|---|---|---|---|
| 4,256,094 A | * | 3/1981 | Kapp | A61B 5/022 600/488 |
| 5,487,760 A | | 1/1996 | Villafana | |
| 6,030,335 A | * | 2/2000 | Franchi | A61M 1/1037 600/16 |
| 6,030,336 A | * | 2/2000 | Franchi | A61M 1/106 600/16 |
| 6,050,932 A | * | 4/2000 | Franchi | A61M 1/1072 600/16 |
| 7,643,879 B2 | | 1/2010 | Shuros et al. | |
| 7,914,569 B2 | | 3/2011 | Nguyen et al. | |

(Continued)

FOREIGN PATENT DOCUMENTS

| | | |
|---|---|---|
| FR | 3034650 | 10/2016 |
| WO | 2014/043235 | 3/2014 |
| WO | 2016/157183 | 10/2016 |

OTHER PUBLICATIONS

"Pacing at the Bundle of His," Medtronic, Inc., Minneapolis, MN, USA (Oct. 2017).

(Continued)

*Primary Examiner* — Alvin J Stewart
(74) *Attorney, Agent, or Firm* — Sughrue Mion, PLLC

(57) ABSTRACT

A method of assembling an electronic prosthetic aortic valve is provided. The method includes inserting an electronics component into a valve component, the electronics component including one or more electrodes and a prosthetic-valve coil, and the valve component including a frame and prosthetic leaflets coupled to the frame; and coupling the electronics component to the valve component. Other embodiments are also described.

24 Claims, 6 Drawing Sheets

(56) References Cited

U.S. PATENT DOCUMENTS

| | | | |
|---|---|---|---|
| 8,092,365 B2* | 1/2012 | Rinderknecht | A61M 1/12 417/394 |
| 9,005,106 B2 | 4/2015 | Gross et al. | |
| 9,326,854 B2 | 5/2016 | Casley et al. | |
| 9,526,637 B2* | 12/2016 | Dagan | A61F 2/915 |
| 9,662,211 B2* | 5/2017 | Hodson | G01M 99/00 |
| 9,737,264 B2* | 8/2017 | Braido | A61B 5/6862 |
| 9,808,201 B2* | 11/2017 | Braido | A61F 2/2412 |
| 2003/0032853 A1* | 2/2003 | Korakianitis | A61M 1/1086 600/16 |
| 2004/0024285 A1* | 2/2004 | Muckter | A61M 1/101 600/16 |
| 2004/0097784 A1* | 5/2004 | Peters | A61M 1/1072 600/18 |
| 2004/0111006 A1* | 6/2004 | Alferness | A61F 2/06 600/16 |
| 2005/0049696 A1* | 3/2005 | Siess | A61F 2/2427 623/2.11 |
| 2010/0197994 A1* | 8/2010 | Mehmanesh | A61M 1/1072 600/18 |
| 2011/0071351 A1* | 3/2011 | Sperling | A61F 2/2472 600/109 |
| 2011/0137370 A1* | 6/2011 | Gross | A61M 1/1072 607/44 |
| 2011/0196482 A1* | 8/2011 | Forsell | A61F 2/2403 623/2.17 |
| 2012/0245678 A1* | 9/2012 | Solem | A61M 1/1081 623/2.36 |
| 2013/0138205 A1* | 5/2013 | Kushwaha | A61M 1/127 623/1.26 |
| 2013/0297009 A1* | 11/2013 | Chalekian | A61F 2/2481 623/2.1 |
| 2014/0066895 A1 | 3/2014 | Kipperman | |
| 2014/0081154 A1* | 3/2014 | Toth | A61B 5/6862 600/479 |
| 2014/0180391 A1 | 6/2014 | Dagan et al. | |
| 2014/0275720 A1* | 9/2014 | Ferrari | A61B 5/0402 600/16 |
| 2015/0128684 A1* | 5/2015 | Hodson | G01M 99/00 73/37 |
| 2016/0045165 A1 | 2/2016 | Braido et al. | |
| 2016/0045316 A1* | 2/2016 | Braido | A61B 5/6862 623/2.38 |
| 2016/0144091 A1* | 5/2016 | Breedon | A61F 2/0036 623/3.29 |
| 2016/0278951 A1* | 9/2016 | Dagan | A61F 2/915 |
| 2017/0100527 A1* | 4/2017 | Schwammenthal | A61M 1/1024 |
| 2017/0258585 A1 | 9/2017 | Marquez et al. | |
| 2017/0266433 A1 | 9/2017 | Daniels et al. | |
| 2019/0076588 A1* | 3/2019 | Ochsner | A61M 1/1086 |

OTHER PUBLICATIONS

"Medtronic Evolut™ PRO System brochure," Medtronic, Inc., Minneapolis, MN, USA (Mar. 2017).

"Medtronic CoreValve™ System Instructions for Use," Medtronic, Inc., Minneapolis, MN, USA (2014).

An Extended European Search Report in corresponding European Appl. No. 19150581.7, dated May 17, 2019.

* cited by examiner

PROSTHETIC AORTIC VALVE PACING SYSTEM

FIELD OF THE APPLICATION

The present invention relates generally to surgical implants and systems, and specifically to prosthetic aortic valves and systems.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset cardiac conduction disturbances are common after transcatheter aortic valve implantation (TAVI). The most common complication is left bundle branch block (LBBB).

U.S. Pat. No. 7,914,569 to Nguyen et al., which is incorporated herein by reference, describes a heart valve prosthesis having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

SUMMARY OF THE APPLICATION

Some embodiments of the present invention provide a prosthetic aortic valve, which comprises a plurality of prosthetic leaflets, a frame, and one or more electrodes coupled to the frame. The frame is shaped so as to define an upstream inflow portion; a downstream outflow portion; and a constriction portion, which is axially between the upstream inflow portion and the downstream outflow portion. The prosthetic leaflets are coupled to the constriction portion. When the prosthetic aortic valve is in an expanded fully-deployed configuration: free edges of the prosthetic leaflets face toward the downstream outflow portion, and a ring-shaped longitudinal border between the downstream outflow portion and the constriction portion is defined by a downstream-most point of the frame to which the prosthetic leaflets are coupled. The prosthetic aortic valve further comprises a prosthetic-valve coil, which is in non-wireless electrical communication with the one or more electrodes, and which is coupled to the frame no more than 1 mm upstream of the ring-shaped longitudinal border, such as axially along the downstream outflow portion.

There is therefore provided, in accordance with an Inventive concept 1 of the present invention, a method of assembling an electronic prosthetic aortic valve, the method including:

inserting an electronics component into a valve component, the electronics component including one or more electrodes and a prosthetic-valve coil, and the valve component including a frame and prosthetic leaflets coupled to the frame; and coupling the electronics component to the valve component.

Inventive concept 2. The method according to Inventive concept 1, wherein coupling the electronics component to the valve component includes:

coupling a first portion of the electronics component to an inner surface of the frame; and coupling a second portion of the electronics component to an external surface of the frame.

Inventive concept 3. The method according to Inventive concept 2, wherein the first portion of the electronics component includes the prosthetic-valve coil and one of the one or more electrodes, and wherein the second portion of the electronics component includes a cathode of the one or more electrodes.

Inventive concept 4. The method according to Inventive concept 3, wherein the electronics component further includes prosthetic-aortic-valve control circuitry, and wherein the first portion of the electronic component includes the prosthetic-aortic-valve control circuitry.

Inventive concept 5. The method according to Inventive concept 4, wherein the electronics component further includes an elongate insulated electrical conductor that electrically couples the cathode to the prosthetic-aortic-valve control circuitry, and wherein coupling the electronics component to the valve component includes coupling the electronics component to the valve component such that the conductor passes from inside to outside the frame.

Inventive concept 6. The method according to Inventive concept 5, wherein the valve component further includes a skirt, and wherein coupling the electronics component to the valve component includes coupling the electronics component to the valve component such that the conductor passes from inside to outside the frame through the skirt.

Inventive concept 7. The method according to Inventive concept 1, wherein coupling the electronics component to the valve component includes stitching the electronics component to the valve component.

Inventive concept 8. The method according to Inventive concept 1, wherein the valve component further includes a skirt, and wherein coupling the electronics component to the valve component includes stitching the electronics component to the skirt.

There is further provided, in accordance with an Inventive concept 9 of the present invention, apparatus including a prosthetic aortic valve, which includes:

(a) a plurality of prosthetic leaflets;
(b) a frame, which is shaped so as to define:
  (1) an upstream inflow portion,
  (2) a downstream outflow portion, and
  (3) a constriction portion, which is axially between the upstream inflow portion and the downstream outflow portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;
(c) one or more electrodes coupled to the frame; and
(d) a prosthetic-valve coil, which is in non-wireless electrical communication with the one or more electrodes, and which is coupled to the frame no more than 1 mm upstream of the ring-shaped longitudinal border.

Inventive concept 10. The apparatus according to Inventive concept 9, wherein the prosthetic-valve coil is disposed axially along the downstream outflow portion.

Inventive concept 11. The apparatus according to Inventive concept 9, wherein at least one of the one or more electrodes is coupled to the upstream inflow portion of the frame.

Inventive concept 12. The apparatus according to Inventive concept 11, wherein when the prosthetic aortic valve is in the expanded fully-deployed configuration:

the frame has an inflow end at the upstream inflow portion and a downstream outflow end at the downstream outflow portion, and an axial length, measured between the inflow end and the downstream outflow end, and at least one of the one or more electrodes is coupled to the upstream inflow portion within a distance from the inflow end, the distance equal to 10% of the axial length of the frame.

Inventive concept 13. The apparatus according to Inventive concept 9, the valve prosthesis system further includes an external unit, which includes:

an external-unit coil; and external-unit control circuitry, which is configured to drive the external-unit coil to wirelessly transfer energy, by inductive coupling, to the prosthetic-valve coil when the prosthetic aortic valve is in the expanded fully-deployed configuration.

Inventive concept 14. The apparatus according to Inventive concept 13, wherein the external-unit control circuitry is configured to drive the one or more electrodes to apply a pacing signal.

Inventive concept 15. The apparatus according to Inventive concept 13, wherein the external unit includes a collar configured to be worn around a patient's neck, and the external-unit coil is incorporated into the collar.

Inventive concept 16. The apparatus according to Inventive concept 9, wherein the prosthetic aortic valve further includes prosthetic-aortic-valve control circuitry, which is coupled to the frame and which is in non-wireless electrical communication with the one or more electrodes, and wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 17. The apparatus according to Inventive concept 16, wherein the prosthetic-aortic-valve control circuitry is configured to apply pacing.

Inventive concept 18. The apparatus according to Inventive concept 16, wherein the one or more electrodes include a cathode that is coupled to the upstream inflow portion of the frame, and wherein the prosthetic-aortic-valve control circuitry is configured to drive the cathode to apply a cathodic current.

Inventive concept 19. The apparatus according to Inventive concept 18, wherein the prosthetic aortic valve further includes a skirt coupled to an external surface of the upstream inflow portion of the frame, and wherein the cathode is disposed on an external surface of the skirt.

Inventive concept 20. The apparatus according to Inventive concept 16, wherein the prosthetic leaflets are coupled to the frame at at least first and second commissures that are located at respective first and second angular locations around the frame separated by a first angular offset around the frame when the prosthetic aortic valve is in the expanded fully-deployed configuration, and wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive concept 21. The apparatus according to Inventive concept 16, wherein the prosthetic-aortic-valve control circuitry is coupled to the frame inside the frame.

Inventive concept 22. The apparatus according to Inventive concept 16, wherein the prosthetic-aortic-valve control circuitry is stitched to the frame.

Inventive concept 23. The apparatus according to Inventive concept 16, wherein the prosthetic aortic valve further includes a skirt coupled to an external surface of the upstream inflow portion of the frame, and wherein the prosthetic-aortic-valve control circuitry is stitched to the skirt.

Inventive concept 24. The apparatus according to Inventive concept 16, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive concept 25. The apparatus according to Inventive concept 16, wherein the prosthetic aortic valve includes an electronic implant, which includes:

the prosthetic-aortic-valve control circuitry; and a multi-layer protective coating, which includes the following layers in the following order:

a first inner aluminum oxide (AlOx) film layer deposited on the circuitry; and a second parylene layer deposited on the first inner AlOx film layer, wherein the prosthetic-aortic-valve control circuitry is not encased in a case.

There is still further provided, in accordance with an Inventive concept 26 of the present invention, apparatus including an electronic implant, which includes:

circuitry; and a multi-layer protective coating, which includes the following layers in the following order:

a first inner aluminum oxide (AlOx) film layer deposited on the circuitry; and a second parylene layer deposited on the first inner AlOx film layer, wherein the circuitry is not encased in a case.

Inventive concept 27. The apparatus according to Inventive concept 26, wherein the multi-layer protective coating further includes a third layer disposed on the second parylene layer, the third layer having a thickness of between 100 and 200 microns, and configured to provide mechanical protection for the circuitry.

Inventive concept 28. The apparatus according to Inventive concept 27, wherein the third layer includes a material selected from the group consisting of: silicone and PTFE.

Inventive concept 29. The apparatus according to Inventive concept 27, wherein the third layer is cast onto the second parylene layer.

Inventive concept 30. The apparatus according to Inventive concept 27, wherein the multi-layer protective coating further includes a fourth outer parylene layer deposited on the third layer.

Inventive concept 31. The apparatus according to Inventive concept 26, further including a prosthetic aortic valve, which includes:
  a frame;
  a plurality of prosthetic leaflets coupled to the frame;
  one or more electrodes coupled to the frame; and
  a prosthetic-valve coil coupled to the frame,
  wherein the electronic implant is coupled to the frame and is in non-wireless electrical communication with the one or more electrodes, and
  wherein the prosthetic-valve coil is in non-wireless electrical communication with the circuitry, such that the prosthetic-valve coil is in non-wireless electrical communication with the one or more electrodes via the circuitry.

There is additionally provided, in accordance with an Inventive concept 32 of the present invention, a method of manufacturing an electronic implant, the method including:
  depositing a first inner aluminum oxide (AIOx) film layer on circuitry of the electronic implant; and
  depositing a second parylene layer on the first inner AIOx film layer, so as to form a multi-layer protective coating with the first inner AIOx film layer,
  wherein manufacturing the electronic implant does not include encasing the circuitry in a case.

Inventive concept 33. The method according to Inventive concept 32, further including disposing a third layer on the second parylene layer, the third layer having a thickness of between 100 and 200 microns, and configured to provide mechanical protection for the circuitry.

Inventive concept 34. The method according to Inventive concept 33, wherein the third layer includes a material selected from the group consisting of: silicone and PTFE.

Inventive concept 35. The method according to Inventive concept 33, wherein disposing the third layer includes casting the third layer onto the second parylene layer.

Inventive concept 36. The method according to Inventive concept 33, further including depositing a fourth outer parylene layer on the third layer.

There is yet additionally provided, in accordance with an Inventive concept 37 of the present invention, apparatus including a prosthetic aortic valve, which includes:
  (a) a plurality of prosthetic leaflets;
  (b) a frame, which is shaped so as to define:
    (1) an upstream inflow portion,
    (2) a downstream outflow portion, and
    (3) a constriction portion, which is axially between the upstream inflow portion and the downstream outflow portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;
  (c) one or more electrodes coupled to the upstream inflow portion of the frame; and
  (d) a prosthetic-valve coil, which is in non-wireless electrical communication with the one or more electrodes.

Inventive concept 38. The apparatus according to Inventive concept 37, wherein when the prosthetic aortic valve is in the expanded fully-deployed configuration:
  the frame has an inflow end at the upstream inflow portion and a downstream outflow end at the downstream outflow portion, and an axial length, measured between the inflow end and the downstream outflow end, and
  at least one of the one or more electrodes is coupled to the upstream inflow portion within a distance from the inflow end, the distance equal to 10% of the axial length of the frame.

Inventive concept 39. The apparatus according to Inventive concept 37,
  wherein the prosthetic aortic valve further includes prosthetic-aortic-valve control circuitry, which is coupled to the frame and which is in non-wireless electrical communication with the one or more electrodes, and
  wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 40. The apparatus according to Inventive concept 39, wherein the prosthetic-aortic-valve control circuitry is configured to apply pacing.

Inventive concept 41. The apparatus according to Inventive concept 39,
  wherein the one or more electrodes include a cathode that is coupled to the upstream inflow portion of the frame, and
  wherein the prosthetic-aortic-valve control circuitry is configured to drive the cathode to apply a cathodic current.

Inventive concept 42. The apparatus according to Inventive concept 41, wherein the prosthetic aortic valve further includes a skirt coupled to an external surface of the upstream inflow portion of the frame, and wherein the cathode is disposed on an external surface of the skirt.

There is also provided, in accordance with an Inventive concept 43 of the present invention, a method of assembling an electronic prosthetic aortic valve, the method including:
  inserting an electronics component into a valve component, the electronics component including one or more electrodes and a prosthetic-valve coil, and the valve component including a frame and prosthetic leaflets coupled to the frame; and
  coupling the electronics component to the valve component.

Inventive concept 44. The method according to Inventive concept 43, wherein coupling the electronics component to the valve component includes:
  coupling a first portion of the electronics component to an inner surface of the frame; and
  coupling a second portion of the electronics component to an external surface of the frame.

Inventive concept 45. The method according to Inventive concept 44,
  wherein the first portion of the electronics component includes the prosthetic-valve coil and one of the one or more electrodes, and
  wherein the second portion of the electronics component includes a cathode of the one or more electrodes.

Inventive concept 46. The method according to Inventive concept 45, wherein the electronics component further includes prosthetic-aortic-valve control circuitry, and wherein the first portion of the electronic component includes the prosthetic-aortic-valve control circuitry.

Inventive concept 47. The method according to Inventive concept 46,
  wherein the electronics component further includes an elongate insulated electrical conductor that electrically couples the cathode to the prosthetic-aortic-valve control circuitry, and wherein coupling the electronics component to the valve component includes coupling the electronics component to the valve component such that the conductor passes from inside to outside the frame.

Inventive concept 48. The method according to Inventive concept 47, wherein the valve component further includes a skirt, and wherein coupling the electronics component to the valve component includes coupling the electronics component to the valve component such that the conductor passes from inside to outside the frame through the skirt.

Inventive concept 49. The method according to Inventive concept 43, wherein coupling the electronics component to the valve component includes stitching the electronics component to the valve component.

Inventive concept 50. The method according to Inventive concept 43, wherein the valve component further includes a skirt, and wherein coupling the electronics component to the valve component includes stitching the electronics component to the skirt.

There is further provided, in accordance with an Inventive concept 51 of the present invention, apparatus including a valve prosthesis system including:
- (a) a delivery system, which includes:
  a delivery tube;
  a delivery-system coil, which is coupled to the delivery tube at a distal site of the delivery tube;
  one or more wires, which pass along the delivery tube; and
  delivery-system control circuitry, which is in electrical communication with the delivery-system coil via the one or more wires; and
- (b) a prosthetic aortic valve, which includes:
  a frame;
  a plurality of prosthetic leaflets coupled to the frame;
  one or more electrodes coupled to the frame; and
  a prosthetic-valve coil coupled to the frame and in non-wireless electrical communication with the one or more electrodes, wherein the prosthetic aortic valve is (i) removably disposable in the delivery tube in a compressed delivery configuration and (ii) configured to assume:
- (A) a partially-expanded partially-deployed configuration upon being partially released from a distal end of the delivery tube such that (1) at least one of the one or more electrodes is positioned outside the delivery tube, and (2) the prosthetic-valve coil is compressed within the delivery tube, and
- (B) an expanded fully-deployed configuration upon being fully released from the distal end of the delivery tube, and wherein the delivery-system control circuitry is configured to drive the delivery-system coil to wirelessly transfer energy, by inductive coupling, to the prosthetic-valve coil at least when the prosthetic aortic valve is in the partially-deployed configuration.

Inventive concept 52. The apparatus according to Inventive concept 51, the valve prosthesis system further includes an external unit, which includes:
  an external-unit coil; and
  external-unit control circuitry, which is configured to drive the external-unit coil to wirelessly transfer energy, by inductive coupling, to the prosthetic-valve coil when the prosthetic aortic valve is in the expanded fully-deployed configuration.

Inventive concept 53. The apparatus according to Inventive concept 52, wherein the external-unit control circuitry is configured to begin driving the external-unit coil to wirelessly transfer the energy only after the prosthetic aortic valve is in the expanded fully-deployed configuration.

Inventive concept 54. The apparatus according to Inventive concept 51, wherein the delivery-system control circuitry is configured to cease driving the delivery-system coil to wirelessly transfer the energy when the prosthetic aortic valve assumes the expanded fully-deployed configuration upon being fully released from the distal end of the delivery tube.

Inventive concept 55. The apparatus according to Inventive concept 51,
  wherein the frame is shaped so as to define:
    an upstream inflow portion,
    a downstream outflow portion, and
    a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration, and
  wherein the prosthetic-valve coil is disposed axially along the downstream outflow portion.

Inventive concept 56. The apparatus according to Inventive concept 55, wherein the prosthetic-valve coil is not disposed axially along the constriction portion and is not disposed axially along the upstream inflow portion.

Inventive concept 57. The apparatus according to Inventive concept 55, wherein at least one of the one or more electrodes is coupled to the upstream inflow portion of the frame.

Inventive concept 58. The apparatus according to Inventive concept 57, wherein when the prosthetic aortic valve is in the expanded fully-deployed configuration:
  the frame has an inflow end at the upstream inflow portion and a downstream outflow end at the downstream outflow portion, and an axial length, measured between the inflow end and the downstream outflow end, and
  at least one of the one or more electrodes is coupled to the upstream inflow portion within a distance from the inflow end, the distance equal to 10% of the axial length of the frame.

Inventive concept 59. The apparatus according to Inventive concept 51,
  wherein the prosthetic aortic valve further includes prosthetic-aortic-valve control circuitry, which is coupled to the frame and which is in non-wireless electrical communication with the one or more electrodes, and
  wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 60. The apparatus according to Inventive concept 59,
  wherein the frame is shaped so as to define:
    an upstream inflow portion,
    a downstream outflow portion, and
    a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration,
  wherein the one or more electrodes include a cathode that is coupled to the upstream inflow portion of the frame, and wherein the prosthetic-aortic-valve control circuitry is configured to drive the cathode to apply a cathodic current.

Inventive concept 61. The apparatus according to Inventive concept 60, wherein the prosthetic aortic valve further includes a skirt coupled to an external surface of the upstream inflow portion of the frame, and wherein the cathode is disposed on an external surface of the skirt.

Inventive concept 62. The apparatus according to Inventive concept 59, wherein the prosthetic leaflets are coupled to the frame at at least first and second commissures that are located at respective first and second angular locations around the frame separated by a first angular offset around the frame when the prosthetic aortic valve is in the expanded fully-deployed configuration, and wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive concept 63. The apparatus according to Inventive concept 59, wherein the prosthetic-aortic-valve control circuitry is coupled to the frame inside the frame.

Inventive concept 64. The apparatus according to Inventive concept 59, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive concept 65. The apparatus according to Inventive concept 59, wherein the prosthetic-aortic-valve control circuitry is configured to drive the one or more electrodes to apply rapid ventricular pacing.

Inventive concept 66. The apparatus according to Inventive concept 51, wherein the delivery-system control circuitry is configured to drive the one or more electrodes, via the delivery-system coil and the prosthetic-valve coil, to apply rapid ventricular pacing.

There is still further provided, in accordance with an Inventive concept 67 of the present invention, a method including:

advancing, through vasculature of a patient, a delivery tube of a delivery system of a valve prosthesis system including, until a distal end of the delivery tube is disposed in an ascending aorta of the patient, while a prosthetic aortic valve of the valve prosthesis system is removably disposed in the delivery tube in a compressed delivery configuration, wherein the prosthetic aortic valve includes (a) a frame, (b) a plurality of prosthetic leaflets coupled to the frame, (c) one or more electrodes coupled to the frame, and (d) a prosthetic-valve coil coupled to the frame and in non-wireless electrical communication with the one or more electrodes;

partially releasing the prosthetic aortic valve from the distal end of the delivery tube such that the prosthetic aortic valve assumes a partially-expanded partially-deployed configuration, in which (a) at least one of one or more electrodes is positioned outside the delivery tube, and (b) the prosthetic-valve coil is compressed within the delivery tube;

thereafter, activating delivery-system control circuitry to drive a delivery-system coil to wirelessly transfer energy, by inductive coupling, to the prosthetic-valve coil at least when the prosthetic aortic valve is in the partially-deployed configuration, wherein the delivery-system coil is coupled to the delivery tube at a distal site of the delivery tube, and wherein the delivery-system control circuitry is in electrical communication with the delivery-system coil via one or more wires that pass along the delivery tube; and thereafter, fully releasing the prosthetic aortic valve from the distal end of the delivery tube such that the prosthetic aortic valve assumes an expanded fully-deployed configuration.

Inventive concept 68. The method according to Inventive concept 67, further including, after fully releasing the prosthetic aortic valve from the distal end of the delivery tube, activating external-unit control circuitry of an external unit to drive an external-unit coil to wirelessly transfer energy, by inductive coupling, to the prosthetic-valve coil when the prosthetic aortic valve is in the expanded fully-deployed configuration.

Inventive concept 69. The method according to Inventive concept 67, wherein the delivery-system control circuitry is configured to cease driving the delivery-system coil to wirelessly transfer the energy when the prosthetic aortic valve assumes the expanded fully-deployed configuration upon being fully released from the distal end of the delivery tube.

Inventive concept 70. The method according to Inventive concept 67, wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration, and wherein the prosthetic-valve coil is disposed axially along the downstream outflow portion.

Inventive concept 71. The method according to Inventive concept 70, wherein the prosthetic-valve coil is not disposed axially along the constriction portion or the upstream inflow portion.

Inventive concept 72. The method according to Inventive concept 70, wherein at least one of the one or more electrodes is coupled to the upstream inflow portion of the frame.

Inventive concept 73. The method according to Inventive concept 72, wherein when the prosthetic aortic valve is in the expanded fully-deployed configuration:

the frame has an inflow end at the upstream inflow portion and a downstream outflow end at the downstream outflow portion, and an axial length, measured between the inflow end and the downstream outflow end, and at least one of the one or more electrodes is coupled to the upstream inflow portion within a distance from the inflow end, the distance equal to 10% of the axial length of the frame.

Inventive concept 74. The method according to Inventive concept 67, wherein the prosthetic aortic valve further includes prosthetic-aortic-valve control circuitry, which is coupled to the frame and which is in non-wireless electrical communication with the one or more electrodes, and wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 75. The method according to Inventive concept 74, wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration, wherein the one or more electrodes include a cathode that is coupled to the upstream inflow portion of the frame, and wherein the prosthetic-aortic-valve control circuitry is configured to drive the cathode to apply a cathodic current.

Inventive concept 76. The method according to Inventive concept 74, wherein the prosthetic leaflets are coupled to the frame at at least first and second commissures that are located at respective first and second angular locations around the frame separated by a first angular offset around the frame when the prosthetic aortic valve is in the expanded fully-deployed configuration, and wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive concept 77. The method according to Inventive concept 74, wherein the prosthetic-aortic-valve control circuitry is coupled to the frame inside the frame.

Inventive concept 78. The method according to Inventive concept 74, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive concept 79. The method according to Inventive concept 74, wherein the prosthetic-aortic-valve control circuitry is configured to drive the one or more electrodes to apply rapid ventricular pacing.

Inventive concept 80. The method according to Inventive concept 67, wherein activating the delivery-system control circuitry includes activating the delivery-system control circuitry to drive the one or more electrodes, via the delivery-system coil and the prosthetic-valve coil, to apply rapid ventricular pacing.

The present invention will be more fully understood from the following detailed description of embodiments thereof, taken together with the drawings, in which:

DETAILED DESCRIPTION OF APPLICATIONS

Figure 1A:
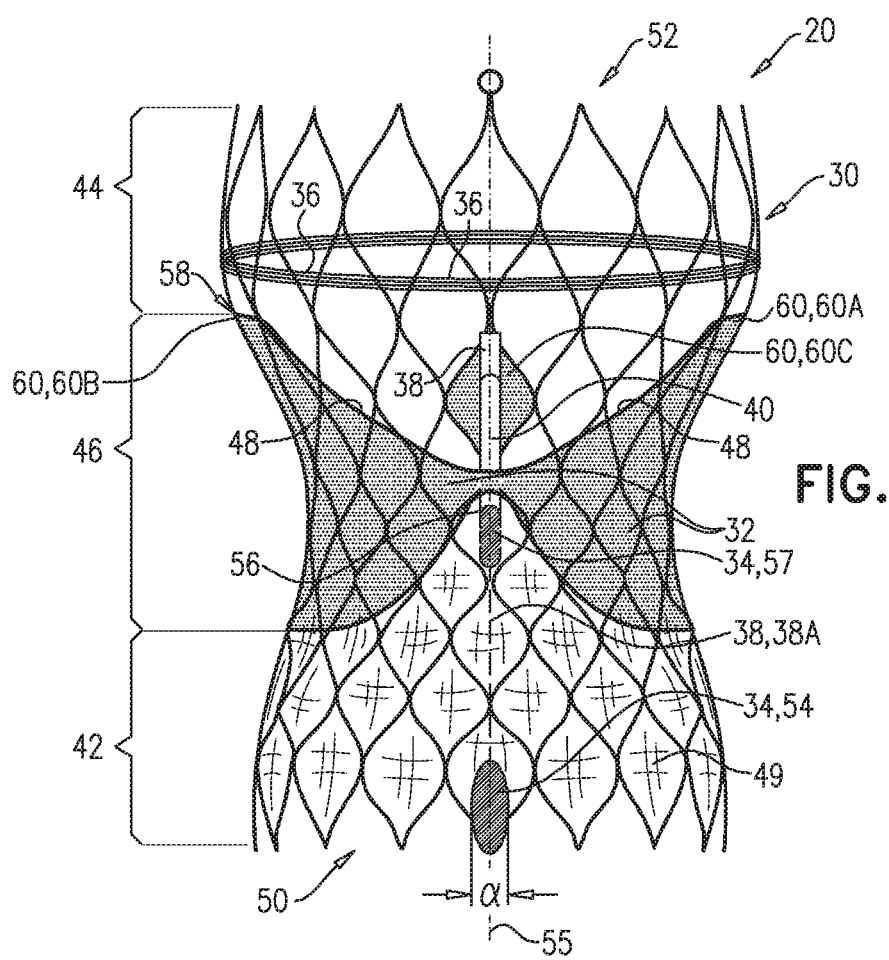
FIGS. 1A and 1B are schematic illustrations of a prosthetic aortic valve, in accordance with an application of the present invention.
Figure 1B:
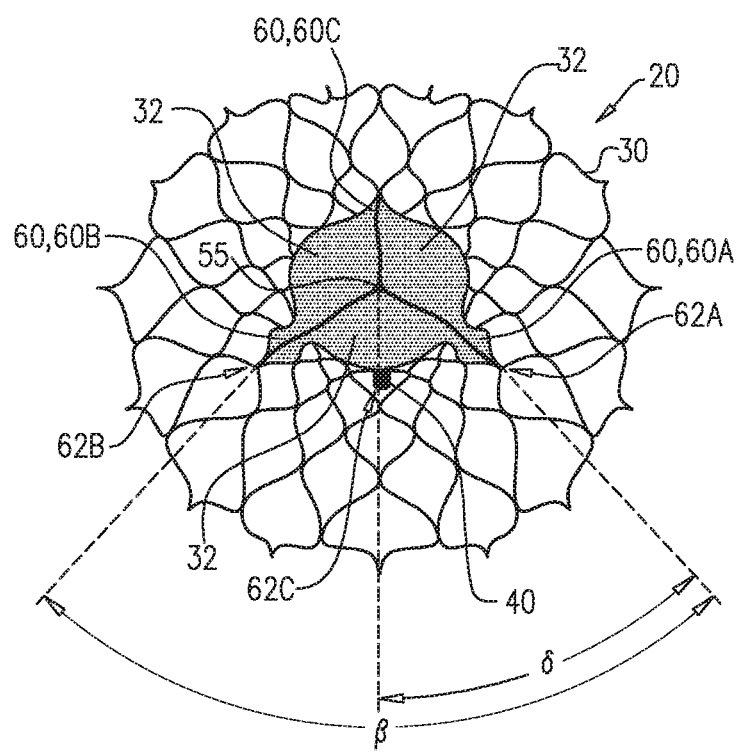

FIGS. 1A and 1B are schematic illustrations of a prosthetic aortic valve 20, in accordance with an application of the present invention. Prosthetic aortic valve 20 is shown in FIGS. 1A-B in an expanded configuration, which is similar to the expanded fully-deployed configuration described hereinbelow with reference to FIG. 3C, except that in FIGS. 1A-B expansion of prosthetic aortic valve 20 is not limited by anatomy of a patient. FIG. 1B is a view of prosthetic aortic valve 20 from a downstream outflow end 52, as described hereinbelow.

Prosthetic aortic valve 20 comprises:
a frame 30;
a plurality of prosthetic leaflets 32 coupled to frame 30;
one or more electrodes 34 coupled to frame 30; and
a prosthetic-valve coil 36 coupled to frame 30 and in non-wireless electrical communication with the one or more electrodes 34, optionally by one or more elongate insulated electrical conductors 38, e.g., wires.

Frame 30 typically comprises a stent or other structure, which is typically self-expanding, and may be formed by laser cutting or etching a metal alloy tube comprising, for example, stainless steel or a shape memory material such as Nitinol. For some applications, one or more of electrodes 34 are coupled to frame 30 using techniques described in U.S. Pat. No. 9,526,637 to Dagan et al. and/or US 2016/0278951 to Dagan et al., both of which are incorporated herein by reference. For some applications, prosthetic-valve coil 36 comprises gold wire, in order to provide low resistance.

For some applications, prosthetic aortic valve 20 further comprises prosthetic-aortic-valve control circuitry 40, which is coupled to frame 30 and which is in non-wireless electrical communication with the one or more electrodes 34. In these applications, prosthetic-valve coil 36 is in non-wireless electrical communication with prosthetic-aortic-valve control circuitry 40, such that prosthetic-valve coil 36 is in non-wireless electrical communication with the one or more electrodes 34 via prosthetic-aortic-valve control circuitry 40. One or more of the one or more electrodes 34 may be directly attached in non-wireless electrical communication to prosthetic-aortic-valve control circuitry 40, and/or may be attached in non-wireless electrical communication to prosthetic-aortic-valve control circuitry 40 by the one or more elongate insulated electrical conductors 38. Typically, prosthetic-aortic-valve control circuitry 40 is flexible, and has a thin, linear packaging, and may implement techniques described hereinbelow with reference to FIG. 4. The thinness of control circuitry 40 allows it to be compressed in a delivery tube during deployment of prosthetic aortic valve 20, without the need to increase the diameter of the delivery tube. In addition, the flexibility of control circuitry 40 prevents damage to the control circuitry when it is crimped when compressed into the delivery tube.

For some applications, frame 30 is shaped so as to define an upstream inflow portion 42, a downstream outflow portion 44, and a constriction portion 46, which is axially between upstream inflow portion 42 and downstream outflow portion 44. Prosthetic leaflets 32 are coupled to constriction portion 46 such that free edges 48 of prosthetic leaflets 32 face toward downstream outflow portion 44 when prosthetic aortic valve 20 is in the expanded fully-deployed configuration described hereinbelow with reference to FIG. 3C. Prosthetic leaflets 32 are not coupled to downstream outflow portion 44; therefore, a ring-shaped longitudinal border 58 between downstream outflow portion 44 and constriction portion 46 is defined by a downstream-most point of frame 30 to which prosthetic leaflets 32 are coupled (for example, prosthetic leaflets 32 may be coupled to the downstream-most point of frame 30 at commissures 60, described immediately hereinbelow). (Ring-shaped longitudinal border 58 is at the same longitudinal location around frame 30.) Typically, prosthetic aortic valve 20 further comprises a skirt 49 coupled to upstream inflow portion 42 of frame 30, and prosthetic leaflets 32 are attached along their bases to skirt 49, for example, using sutures or a suitable biocompatible adhesive. Adjoining pairs of leaflets are attached to one another at their lateral ends to form commissures 60, with free edges 48 of the prosthetic leaflets forming coaptation edges that meet one another. Skirt 49 and prosthetic leaflets 32 typically comprise a sheet of animal pericardial tissue, such as porcine pericardial tissue, or synthetic or polymeric material.

For some applications, prosthetic-valve coil 36 is disposed no more than 1 mm upstream of ring-shaped longitudinal border 58 between downstream outflow portion 44 and constriction portion 46, typically axially along downstream outflow portion 44. Such placement allows prosthetic aortic valve 20 to be crimped (compressed) into a delivery tube during deployment of prosthetic aortic valve 20, without requiring a larger-diameter delivery tube to accommodate prosthetic-valve coil 36. This is possible because downstream outflow portion 44 does not include material of prosthetic leaflets 32, and thus can accommodate prosthetic-valve coil 36 without causing downstream outflow portion 44 to have a greater compressed diameter than the other axial portions of prosthetic aortic valve 20. Typically, prosthetic-valve coil 36 is not disposed axially along constriction portion 46 and is not disposed axially along upstream inflow portion 42. In addition, placement of prosthetic-valve coil 36 axially along downstream outflow portion 44 improves transmission efficiency because downstream outflow portion 44 typically has a greater diameter than each of constriction portion 46 and upstream inflow portion 42. In addition, constriction portion 46 typically has a lesser diameter than each of upstream inflow portion 42 and downstream outflow portion 44.

Typically, at least one of the one or more electrodes 34 is coupled to upstream inflow portion 42 of frame 30, such as exactly one of the one or more electrodes 34. For some applications, the one or more electrodes 34 comprise a cathode 54 that is coupled to upstream inflow portion 42 of frame 30, and prosthetic-aortic-valve control circuitry 40 is configured to drive cathode 54 to apply a cathodic current. For some applications, cathode 54 has a lateral dimension a (alpha), measured in degrees around frame 30 with respect to a central longitudinal axis 55 of frame 30, of between 10 and 40 degrees, e.g., between 20 and 40 degrees, such as 30 degrees, in order to accommodate rotational misplacement of frame 30 with respect to the bundle of His. Typically, prosthetic aortic valve 20 is deployed using imaging, such as fluoroscopy, and is rotated if necessary during the deployment such that cathode 54 is disposed against tissue of the annulus that is near the bundle of His. For some applications, prosthetic aortic valve 20 comprises a plurality of cathodes 54 (e.g., two or three, or more), which are disposed at a respective plurality of angular locations around frame 30 (e.g., 10-degrees apart). After implantation of prosthetic aortic valve 20, the cathode 54 that is has the most accurate angular location is activated to apply a pacing signal and/or sense, either by prosthetic-aortic-valve control circuitry 40 or external control circuitry, such as external-unit control circuitry 104, described hereinbelow with reference to FIG. 3C. Alternatively or additionally, for some applications, cathode 54 has an axial length of at least 10 mm, in order to accommodate axial misplacement of frame 30 with respect to the annulus of the natural aortic valve, and thus with respect to the bundle of His. As used in the present application, including in the claims, an "axial length" is a length of a structure measured along central longitudinal axis 55.

For some applications, cathode 54 has a thickness of between 75 and 125 microns, e.g., about 100 microns, and/or a surface area of at least 2.5 mm2, in order to provide adequate stimulation. For some applications, cathode 54 comprises titanium nitride (TiN). For some applications, skirt 49 is coupled to an external surface of upstream inflow portion 42 of frame 30, and cathode 54 is disposed on an external surface of skirt 49. As used in the present application, including in the claims, the "central longitudinal axis" 55 of frame 30 is the set of all centroids of transverse cross-sectional sections of frame 30 along frame 30. Thus the cross-sectional sections are locally perpendicular to the central longitudinal axis, which runs along frame 30. (For applications in which frame 30 is circular in cross-section, the centroids correspond with the centers of the circular cross-sectional sections.)

For some applications, when prosthetic aortic valve is in the expanded fully-deployed configuration described hereinbelow with reference to FIG. 3C:
  frame 30 has an inflow end 50 at upstream inflow portion 42 and downstream outflow end 52 at downstream outflow portion 44, and an axial length, measured between inflow end 50 and downstream outflow end 52, and
  at least one of (e.g., exactly one of, e.g., cathode 54) the one or more electrodes 34 is coupled to upstream inflow portion 42 within a distance from inflow end 50, the distance equal to 10% of the axial length of frame 30 (the distance is measured (a) along central longitudinal axis 55 of frame 30 when in the expanded fully-deployed configuration, and (b) between inflow end 50 and an upstream-most point of the at least one electrode).

Typically, prosthetic-aortic-valve control circuitry 40 is coupled to frame 30 such that upstream-most point of prosthetic-aortic-valve control circuitry 40 is disposed axially along constriction portion 46 and/or downstream outflow portion 44 of frame 30.

Typically, prosthetic-aortic-valve control circuitry 40 is coupled to frame 30 inside frame 30, which may prevent friction between prosthetic-aortic-valve control circuitry 40 and delivery tube 72 during deployment of prosthetic aortic valve 20, described hereinbelow with reference to FIGS. 3A-C. It is noted that for applications in which upstream-most point 56 is disposed no more upstream than 1 mm upstream of ring-shaped longitudinal border 58, such as described above, there is generally enough space inside frame 30 to accommodate prosthetic-aortic-valve control circuitry 40.

For some applications, prosthetic leaflets 32 are coupled to frame 30 at at least first and second commissures 60A and 60B of prosthetic aortic valve 20 that are located at respective first and second angular locations 62A and 62B around frame 30. The first and second angular locations 62A and 62B are separated by a first angular offset β (beta) around frame 30 when prosthetic aortic valve 20 is in the expanded fully-deployed configuration described hereinbelow with reference to FIG. 3C. Prosthetic-aortic-valve control circuitry 40 is coupled to frame 30 at a third angular location 62C around frame 30 that is separated from first angular location 62A by a second angular offset δ (delta) that equals between 40% and 60% (e.g., 50%) of the first angular offset β (beta) when prosthetic aortic valve 20 is in the expanded fully-deployed configuration described hereinbelow with reference to FIG. 3C. At the third angular location 62C around frame 30, the frame is more flexible than at the more rigid commissures. As used in the present application, including in the claims, an "angular location" is a location on frame 30 at a particular location around central longitudinal axis 55, i.e., at a particular "o'clock" with respect to central longitudinal axis 55. (It is noted that a third commissures 60C is shown in FIG. 1A on the far side of the frame, i.e., 180 degrees from circuitry 40.)

Figure 2:
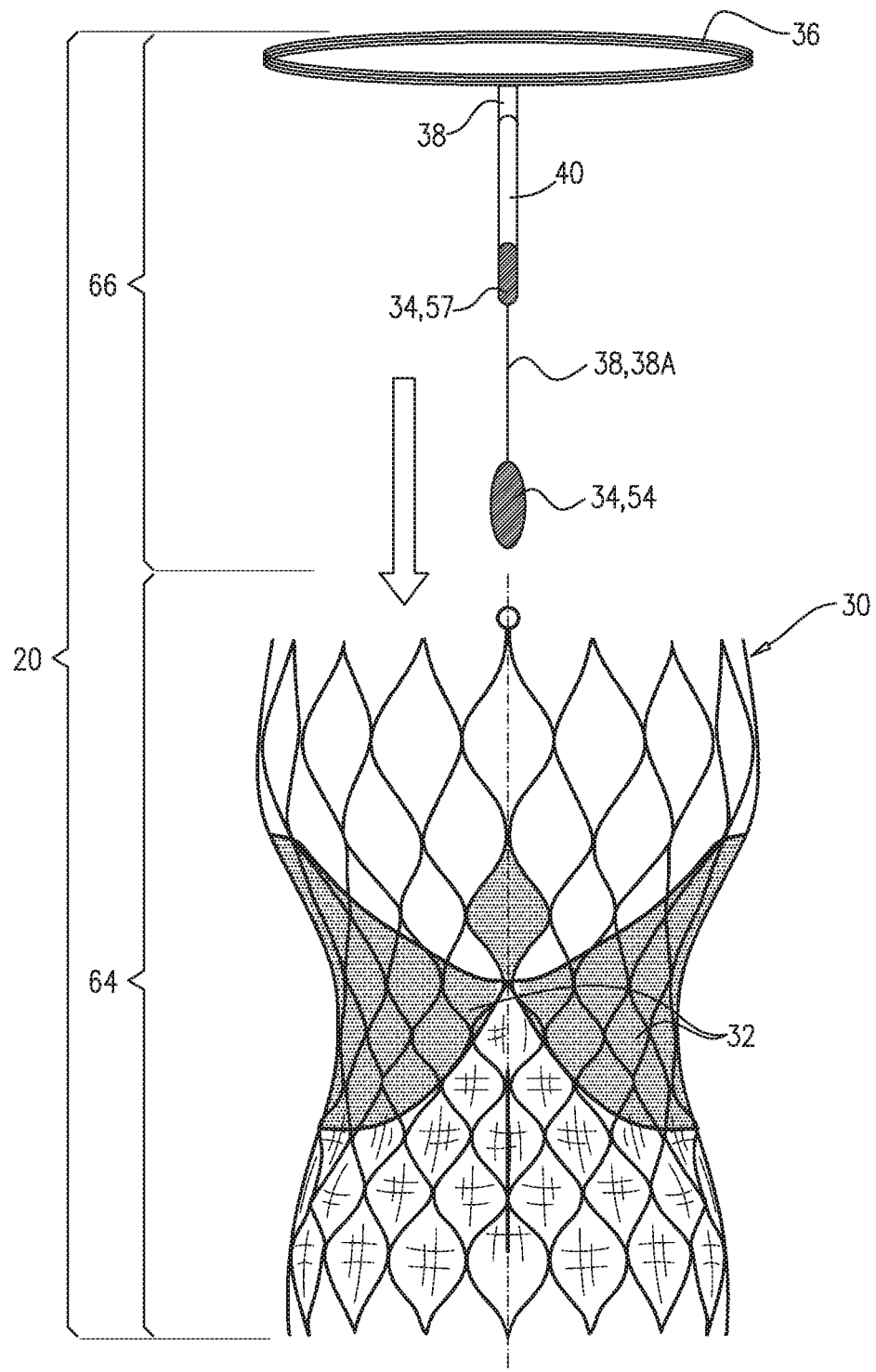
FIG. 2 is a schematic illustration of components of the prosthetic aortic valve of FIGS. 1A-B before complete assembly, in accordance with an application of the present invention.

Reference is now made to FIG. 2, which is a schematic illustration of components of prosthetic aortic valve 20 before complete assembly, in accordance with an application of the present invention. The components comprise a valve component 64 and an electronics component 66. Valve component 64 typically consists of a heart valve prosthesis known in the art, which comprises at least frame 30 and prosthetic leaflets 32. For example, the known heart valve prosthesis may comprise a CoreValve™ Evolut™ R prothesis (Medtronic, Inc., Minneapolis, Minn., USA), a CoreValve™ Evolut™ PRO prosthesis (Medtronic, Inc.), a LOTUS Edge™ Aortic Valve (Boston Scientific Corporation, Marlborough, Mass., USA), or an ACURATE Neo™ Aortic Valve (Boston Scientific Corporation). Electronics component 66 comprises at least the one or more electrodes 34 and prosthetic-valve coil 36, and optionally prosthetic-aortic-valve control circuitry 40.

During assembly of prosthetic aortic valve 20, electronics component 66 is inserted into valve component 64. For some applications, a first portion of electronics component 66, such as prosthetic-valve coil 36, prosthetic-aortic-valve control circuitry 40, and one of the one or more electrodes 34, is coupled to an inner surface of frame 30, and a second portion of electronics component 66, such as cathode 54, is coupled to an external surface of frame 30. For example, one 38A of one or more elongate insulated electrical conductors 38 may electrically couple cathode 54 to prosthetic-aortic-valve control circuitry 40, and the conductor 38A may pass from inside to outside frame 30, typically through skirt 49. Optionally, the components of electronics component 66 may be stitched to frame 30 and/or skirt 49.

Figure 3A:
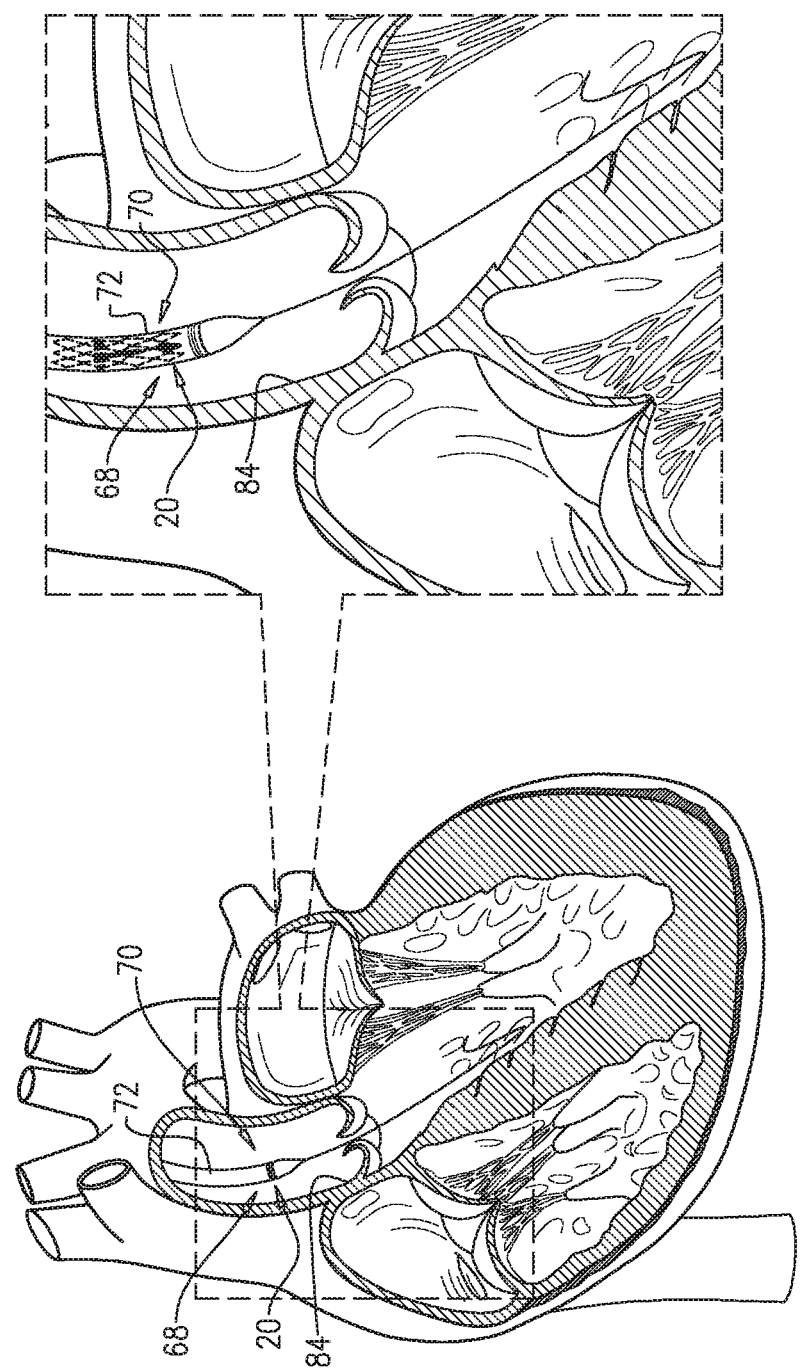
FIGS. 3A-C are schematic illustrations of a valve prosthesis system and a method of using the system, in accordance with respective applications of the present invention.
Figure 3B:
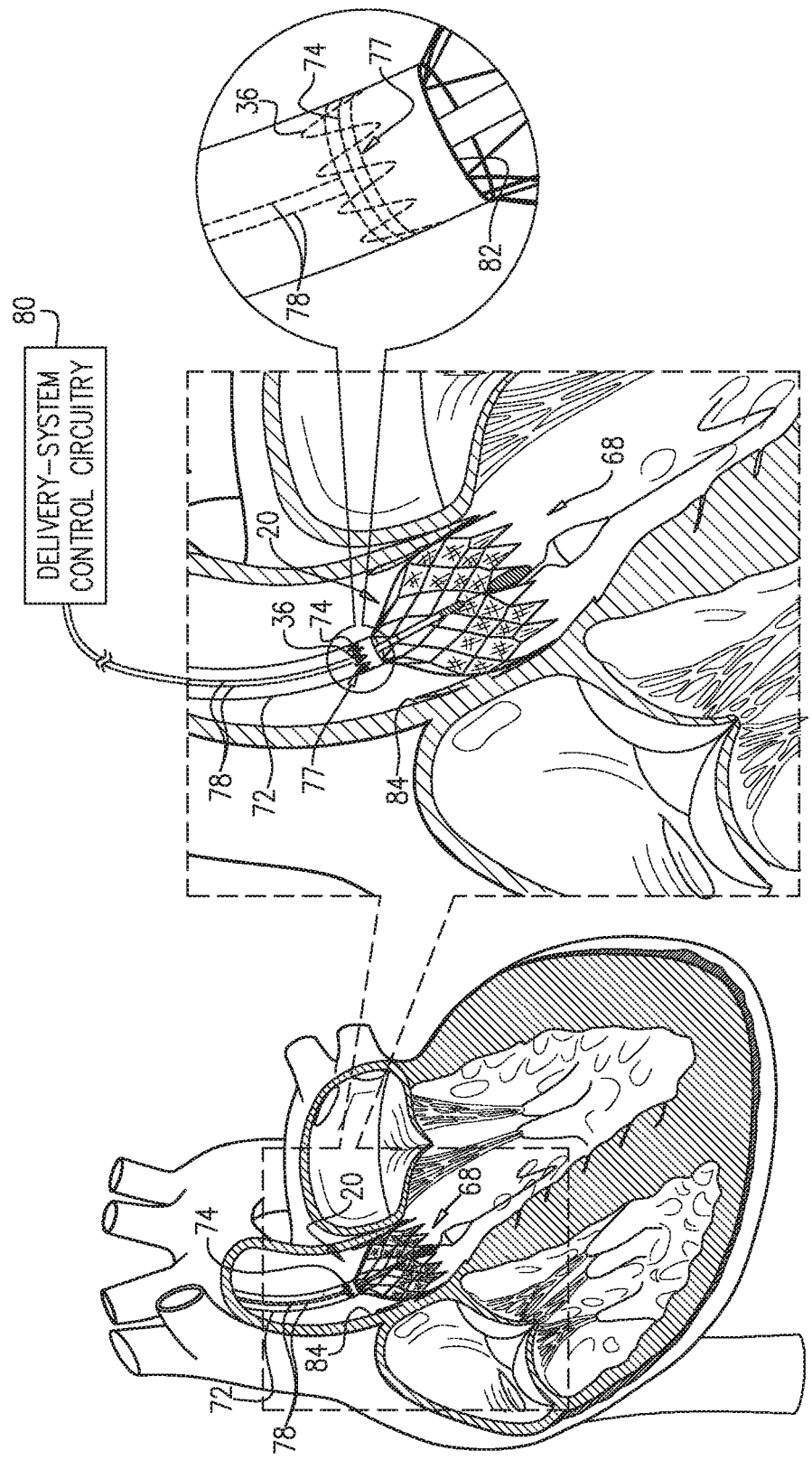
Figure 3C:
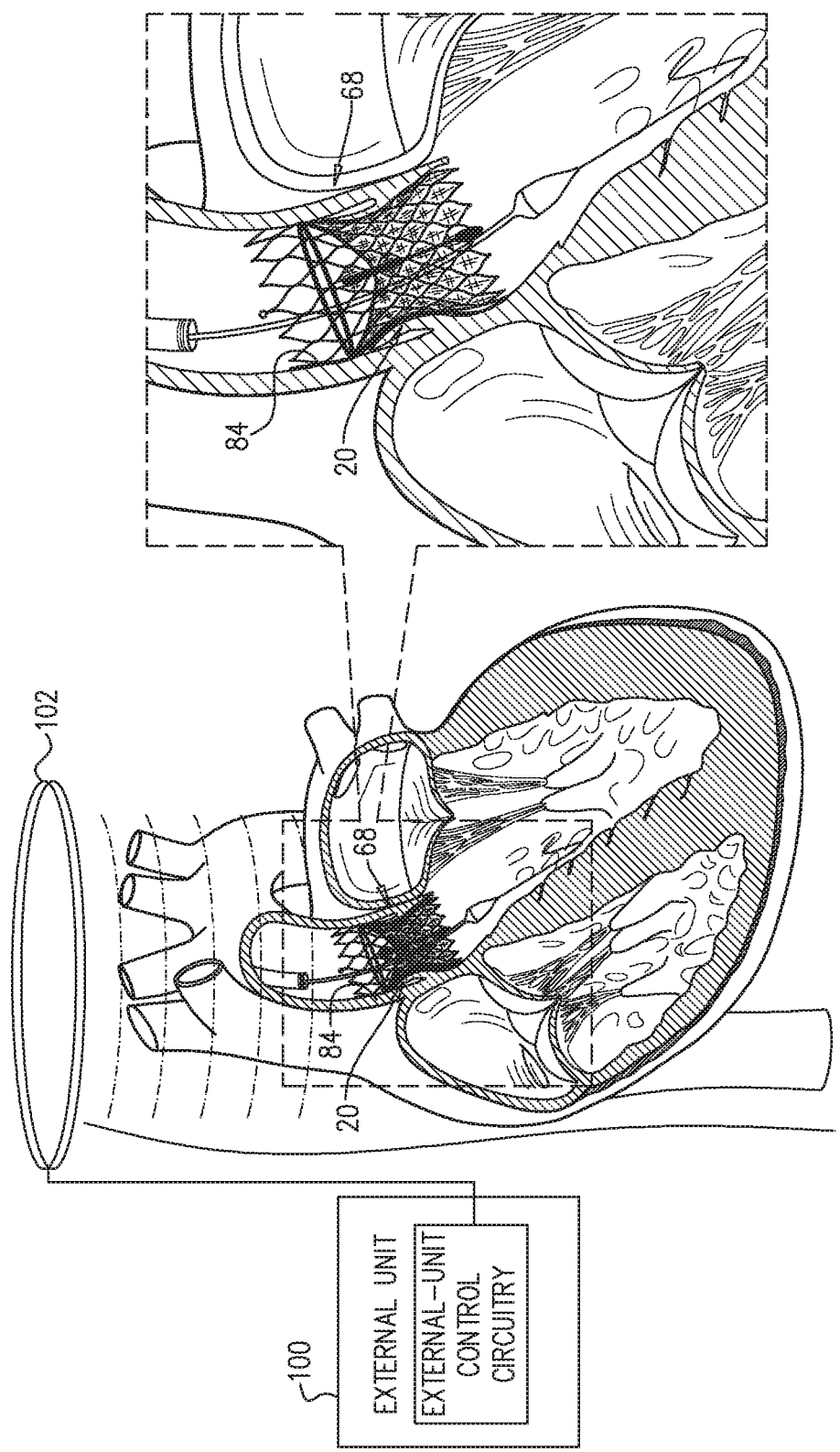

Reference is still made to FIGS. 1A-B and 2, and is additionally made to FIGS. 3A-C, which are schematic illustrations of a valve prosthesis system 68 and a method of using the system, in accordance with respective applications of the present invention. Valve prosthesis system 68 comprises prosthetic aortic valve 20 and a delivery system 70.

Delivery system 70 comprises:
a delivery tube 72;
a delivery-system coil 74, which is coupled to delivery tube 72 at a distal site 76 of delivery tube 72; for example, a distal-most portion 77 of delivery-system coil 74 may be disposed within 10 mm of a distal end 82 of delivery tube 72;
one or more wires 78, which pass along delivery tube 72, e.g., attached to an outer or inner surface of delivery tube 72, or embedded in the wall of delivery tube 72; and
delivery-system control circuitry 80, which is in electrical communication with delivery-system coil 74 via the one or more wires 78.

Delivery-system control circuitry 80 is configured to drive delivery-system coil 74 to wirelessly transfer energy (and, optionally, programming information), by inductive coupling, to prosthetic-valve coil 36 at least when prosthetic aortic valve 20 is in the partially-deployed configuration described hereinbelow with reference to FIG. 3B.

As shown in FIG. 3A, prosthetic aortic valve 20 is removably disposable in delivery tube 72 in a compressed delivery configuration. During an implantation procedure, delivery tube 72 is advanced through vasculature of a patient, until distal end 82 of delivery tube 72 is disposed in an ascending aorta 84 of the patient, while prosthetic aortic valve 20 is removably disposed in delivery tube 72 in the compressed delivery configuration.

As shown in FIG. 3B, prosthetic aortic valve 20 is also configured to assume a partially-expanded partially-deployed configuration upon being partially released from distal end 82 of delivery tube 72 such that (a) at least one of the one or more electrodes 34 is positioned outside delivery tube 72, such as cathode 54, in the vicinity of (e.g., touching) target tissue, such as the natural aortic valve annulus, and (b) prosthetic-valve coil 36 is compressed within delivery tube 72. Typically, delivery-system coil 74 surrounds compressed prosthetic-valve coil 36, which provides high transmission efficiency even though prosthetic-valve coil 36 is still compressed. After prosthetic aortic valve 20 has assumed the partially-expanded partially-deployed configuration, delivery-system control circuitry 80 is activated to drive delivery-system coil 74 to wirelessly transfer energy (and, optionally, programming information), by inductive coupling, to prosthetic-valve coil 36. By contrast, transmission of power from an external coil to compressed prosthetic-valve coil 36 would be quite inefficient because of the greater distance between the transmitting and receiving coils and the compression of prosthetic-valve coil 36.

For some applications, prosthetic-aortic-valve control circuitry 40 is configured to drive the one or more electrodes 34 to apply rapid ventricular pacing. Such pacing may temporary reduce left ventricular output, in order to enable more accurate placement of prosthetic aortic valve 20. Alternatively, delivery-system control circuitry 80 is configured to drive the one or more electrodes 34 to apply the rapid ventricular pacing; in this configuration, prosthetic-aortic-valve control circuitry 40, if even provided, is generally passive, i.e., delivery-system control circuitry 80 sets the parameters of the pacing signal. Alternatively, prosthetic aortic valve 20 is not used for applying rapid ventricular pacing, and may instead be used for applying pacing post-implantation, such as described below, and/or for post-implantation sensing, such as described below.

As described hereinabove with reference to FIGS. 1A-B, for some applications, the one or more electrodes 34 comprise cathode 54 that is coupled to upstream inflow portion 42 of frame 30. When prosthetic aortic valve 20 is in the partially-expanded partially-deployed configuration shown in FIG. 3B, cathode 54 is positioned adjacent to cardiac tissue near the bundle of His, in order to pace the heart by stimulating the cardiac tissue with cathodic current. For some applications, the one or more electrodes further comprise an anode 57, which may be used for bipolar sensing and/or pacing, as known in the art. Typically, cathode 54 and anode 57 are disposed on frame 30 such that there is at least 15 mm between the cathode and the anode, when prosthetic aortic valve 20 is in the expanded fully-deployed configuration described hereinbelow with reference to FIG. 3C (the 15 mm is measured along central longitudinal axis 55 of frame 30 when in the expanded fully-deployed configuration).

As shown in FIG. 3C, prosthetic aortic valve 20 is also configured to assume an expanded fully-deployed configuration upon being fully released from distal end 82 of delivery tube 72. For some applications, delivery-system control circuitry 80 is configured to cease driving delivery-system coil 74 to wirelessly transfer the energy when prosthetic aortic valve 20 assumes the expanded fully-deployed configuration upon being fully released from distal end 82 of delivery tube 72.

For some applications, as shown in FIG. 3C, valve prosthesis system 68 further comprises an external unit 100, which comprises (a) an external-unit coil 102, and (b) external-unit control circuitry 104, which is configured to drive external-unit coil 102 to wirelessly transfer energy (and, optionally, programming information), by inductive coupling, to prosthetic-valve coil 36 when prosthetic aortic valve 20 is in the expanded fully-deployed configuration. In these applications, after prosthetic aortic valve 20 is fully released from distal end 82 of delivery tube 72, external-unit control circuitry 104 is activated to drive external-unit coil 102 to wirelessly transfer energy (and, optionally, programming information), by inductive coupling, to prosthetic-valve coil 36 when prosthetic aortic valve 20 is in the expanded fully-deployed configuration.

For some applications, external-unit coil 102 is incorporated into a collar configured to be worn around the patient's neck, such as described in PCT Publication WO 2016/157183 to Dagan et al., which is incorporated herein by reference. This positioning of external-unit coil 102 provides high transmission efficiency, because the respective axes of external-unit coil 102 and prosthetic-valve coil 36 are generally aligned.

For some applications, prosthetic-aortic-valve control circuitry 40 is configured to use the received energy to drive the one or more electrodes 34 to perform pacing post-implantation, e.g., for several months. Such pacing may employ any standard pacing protocol. For some applications, the pacing is VVI pacing, which is only applied when a QRS complex is not sensed in the ventricle. Alternatively, external-unit control circuitry 104 is configured to drive the one or more electrodes 34 to apply the pacing signal; in this configuration, prosthetic-aortic-valve control circuitry 40, if even provided, is generally passive, i.e., external-unit control circuitry 104 sets the parameters of the pacing signal.

Alternatively, for some applications, prosthetic-aortic-valve control circuitry 40 is configured to (a) use the one or more electrodes 34 to sense a cardiac signal, and (b) drive prosthetic-valve coil 36 to transmit a wireless signal indicative of the sensed cardiac signal. For some applications, the cardiac sensing is performed using techniques described in U.S. Pat. No. 9,005,106 to Gross et al., which is incorporated herein by reference. In these applications, the one or more electrodes 34 are typically not used to apply pacing, any thus need not be configured as a cathode and an anode. Such sensing may enable early discharge of the patient from the hospital after implantation of prosthetic aortic valve 20, before the possible development of left bundle branch block (LBBB). If LBBB develops, as it does in approximately 20-30% of patients, the LBBB is detected by the sensing, an alert is generated, and the LBBB may be treated as appropriate.

Figure 4:
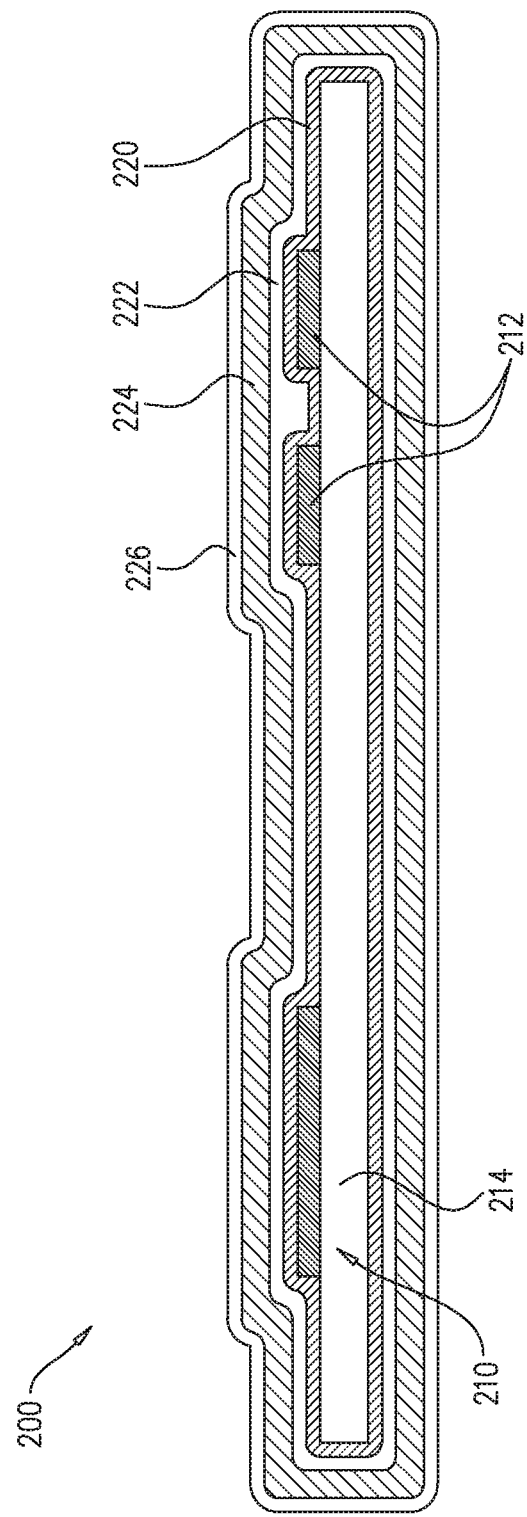
FIG. 4 is a schematic illustration of an electronic implant, in accordance with an application of the present invention.

Reference is now made to FIG. 4, which is a schematic illustration of an electronic implant 200, in accordance with an application of the present invention. Prosthetic-aortic-valve control circuitry 40, described hereinabove with reference to FIGS. 1A-2, may implement features of electronic implant 200.

Electronic implant 200 comprises circuitry 210, which comprises electronic components 212, typically mounted on a long and flexible printed circuit board (PCB) 214. Electronic implant 200 further comprises a multi-layer protective coating, which comprises the following layers in the following order:

a first inner aluminum oxide (AlOx) film layer 220 deposited on circuitry 210, e.g., using atomic layer deposition (ALD);

a second parylene layer 222 deposited (typically, vapor-deposited in a vacuum) on first inner AlOx film layer 220; second parylene layer 222 provides chemical protection for circuitry 210;

optionally, a third layer 224 disposed (typically cast onto) on second parylene layer 222, the third layer, for example, comprising a polymer, such as a polymer selected from the group consisting of: silicone and PTFE; third layer 224 typically has a thickness of between 100 and 200 microns, and is configured to provide mechanical protection for circuitry 210; and optionally, a fourth outer parylene layer 226 deposited (typically, vapor-deposited in a vacuum) on third layer 224; fourth outer parylene layer 226 provides chemical protection for circuitry 210 and third layer 224.

Electronic implant 200 and the layers are drawn highly schematically in FIG. 4, and are not drawn to scale; in particular, the layers are actually much thinner than shown, and the relative thicknesses are different from those shown.

Typically, circuitry 210 is not encased in a case, but is only coated with layers, as described above. A "case" is an enclosure, typically comprising glass and/or metal, that has a structure before circuitry is disposed therein; by contrast, a coating takes the shape of the circuitry to which the coating is applied. By contrast, encasement in a case is standard in the field of implantable circuitry. The lack of such a case allows electronic implant 200 to be thin and flexible, with the tradeoff of shorter lifespan. For prosthetic-aortic-valve control circuitry 40, the shorter lifespan is generally not an issue, because prosthetic-aortic-valve control circuitry 40 is typically only used for several months.

For applications in which prosthetic-aortic-valve control circuitry 40 implements features of electronic implant 200, the one or more electrodes 34 are masked during application of the coatings. Thus, prosthetic-aortic-valve control circuitry 40, the one or more elongate insulated electrical conductors 38 wires, and prosthetic-valve coil 36 are all coated in the same coating procedure.

The techniques described herein for prosthetic aortic valve 20 may be alternatively used, mutatis mutandis, for non-aortic prosthetic valves, such as prosthetic mitral or tricuspid valves.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of assembling an electronic prosthetic aortic valve, the method comprising:

inserting an electronics component into a valve component, the electronics component comprising one or more electrodes and a prosthetic-valve coil, and the valve component comprising a frame and prosthetic leaflets coupled to the frame; and coupling the electronics component to the valve component, wherein coupling the electronics component to the valve component comprises:
coupling a first portion of the electronics component to an inner surface of the frame; and
coupling a second portion of the electronics component to an external surface of the frame.

2. The method according to claim 1,
wherein the first portion of the electronics component comprises the prosthetic-valve coil and one of the one or more electrodes, and
wherein the second portion of the electronics component comprises a cathode of the one or more electrodes.

3. The method according to claim 2, wherein the electronics component further comprises prosthetic-aortic-valve control circuitry, and wherein the first portion of the electronic component comprises the prosthetic-aortic-valve control circuitry.

4. The method according to claim 3,
wherein the electronics component further comprises an elongate insulated electrical conductor that electrically couples the cathode to the prosthetic-aortic-valve control circuitry, and
wherein coupling the electronics component to the valve component comprises coupling the electronics component to the valve component such that the conductor passes from inside to outside the frame.

5. The method according to claim 4, wherein the valve component further comprises a skirt, and wherein coupling the electronics component to the valve component comprises coupling the electronics component to the valve component such that the conductor passes from inside to outside the frame through the skirt.

6. A method of assembling an electronic prosthetic aortic valve, the method comprising:
inserting an electronics component into a valve component, the electronics component comprising one or more electrodes and a prosthetic-valve coil, and the valve component comprising a frame and prosthetic leaflets coupled to the frame; and
coupling the electronics component to the valve component,
wherein coupling the electronics component to the valve component comprises stitching the electronics component to the valve component.

7. The method according to claim 6, wherein the valve component further comprises a skirt, and wherein coupling the electronics component to the valve component comprises stitching the electronics component to the skirt.

8. Apparatus comprising a prosthetic aortic valve, which comprises:
(a) a plurality of prosthetic leaflets;
(b) a frame, which is shaped so as to define:
(1) an upstream inflow portion,
(2) a downstream outflow portion, and
(3) a constriction portion, which is axially between the upstream inflow portion and the downstream outflow portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;
(c) one or more electrodes coupled to the frame; and
(d) a prosthetic-valve coil, which is in non-wireless electrical communication with the one or more electrodes, and which is coupled to the frame no more than 1 mm upstream of the ring-shaped longitudinal border.

9. The apparatus according to claim 8, wherein the prosthetic-valve coil is disposed axially along the downstream outflow portion.

10. The apparatus according to claim 8, wherein at least one of the one or more electrodes is coupled to the upstream inflow portion of the frame.

11. The apparatus according to claim 10, wherein when the prosthetic aortic valve is in the expanded fully-deployed configuration:
the frame has an inflow end at the upstream inflow portion and a downstream outflow end at the downstream outflow portion, and an axial length, measured between the inflow end and the downstream outflow end, and
at least one of the one or more electrodes is coupled to the upstream inflow portion within a distance from the inflow end, the distance equal to 10% of the axial length of the frame.

12. A valve prosthesis system comprising the prosthetic aortic valve according to claim 8, the valve prosthesis system further comprising an external unit, which comprises:
an external-unit coil; and
external-unit control circuitry, which is configured to drive the external-unit coil to wirelessly transfer energy, by inductive coupling, to the prosthetic-valve coil when the prosthetic aortic valve is in the expanded fully-deployed configuration.

13. The valve prosthesis system according to claim 12, wherein the external-unit control circuitry is configured to drive the one or more electrodes to apply a pacing signal.

14. The valve prosthesis system according to claim 12, wherein the external unit comprises a collar configured to be worn around a patient's neck, and the external-unit coil is incorporated into the collar.

15. The valve prosthesis system according to claim 8,
wherein the prosthetic aortic valve further comprises prosthetic-aortic-valve control circuitry, which is coupled to the frame and which is in non-wireless electrical communication with the one or more electrodes, and
wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

16. The valve prosthesis system according to claim 15, wherein the prosthetic-aortic-valve control circuitry is configured to apply pacing.

17. The valve prosthesis system according to claim 15,
wherein the one or more electrodes comprise a cathode that is coupled to the upstream inflow portion of the frame, and
wherein the prosthetic-aortic-valve control circuitry is configured to drive the cathode to apply a cathodic current.

18. The valve prosthesis system according to claim 17, wherein the prosthetic aortic valve further comprises a skirt coupled to an external surface of the upstream inflow portion of the frame, and wherein the cathode is disposed on an external surface of the skirt.

19. The valve prosthesis system according to claim 15, wherein the prosthetic leaflets are coupled to the frame at at least first and second commissures that are located at respective first and second angular locations around the frame separated by a first angular offset around the frame when the prosthetic aortic valve is in the expanded fully-deployed configuration, and
wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

20. The valve prosthesis system according to claim 15, wherein the prosthetic-aortic-valve control circuitry is coupled to the frame inside the frame.

21. The valve prosthesis system according to claim 15, wherein the prosthetic-aortic-valve control circuitry is stitched to the frame.

22. The valve prosthesis system according to claim 15, wherein the prosthetic aortic valve further comprises a skirt coupled to an external surface of the upstream inflow portion of the frame, and wherein the prosthetic-aortic-valve control circuitry is stitched to the skirt.

23. The valve prosthesis system according to claim 15, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

24. The valve prosthesis system according to claim 15, wherein the prosthetic aortic valve comprises an electronic implant, which comprises:
the prosthetic-aortic-valve control circuitry; and
a multi-layer protective coating, which comprises the following layers in the following order:
a first inner aluminum oxide (AlOx) film layer deposited on the circuitry; and
a second parylene layer deposited on the first inner AlOx film layer, wherein the prosthetic-aortic-valve control circuitry is not encased in a case.

* * * * *